United States Patent
Sai et al.

(10) Patent No.: US 8,290,275 B2
(45) Date of Patent: Oct. 16, 2012

(54) EFFECTIVE PIGMENT IDENTIFICATION METHOD, IDENTIFICATION SYSTEM, IDENTIFICATION PROGRAM, AND RECORDING MEDIUM THEREFOR

(75) Inventors: Keisuke Sai, Kanagawa-ken (JP); Yutaka Masuda, Kanagawa-ken (JP); Yoshinori Arai, Kanagawa-ken (JP)

(73) Assignee: Kansai Paint Co., Ltd., Hyogo-Ken (JP)

( * ) Notice: Subject to any disclaimer, the term of this patent is extended or adjusted under 35 U.S.C. 154(b) by 1057 days.

(21) Appl. No.: 11/621,505

(22) Filed: Jan. 9, 2007

(65) Prior Publication Data
US 2007/0172113 A1 Jul. 26, 2007

(30) Foreign Application Priority Data
Jan. 20, 2006 (JP) .................................. 2006-12572

(51) Int. Cl.
G06K 9/00 (2006.01)
G06K 9/46 (2006.01)
G06K 9/32 (2006.01)
G06K 9/62 (2006.01)
G01J 3/46 (2006.01)
G09G 5/02 (2006.01)
H04N 1/46 (2006.01)

(52) U.S. Cl. ........ 382/190; 382/162; 382/305; 382/100; 382/224; 356/402; 345/591; 358/515

(58) Field of Classification Search .................. 382/224, 382/190, 305, 162, 100; 345/591; 358/515; 356/402
See application file for complete search history.

(56) References Cited

U.S. PATENT DOCUMENTS

| | | | | |
|---|---|---|---|---|
| 5,168,352 A * | 12/1992 | Naka et al. | ...................... | 348/34 |
| 5,432,545 A * | 7/1995 | Connolly | ......................... | 348/91 |
| 5,533,628 A * | 7/1996 | Tao | ................................. | 209/580 |
| 5,546,475 A * | 8/1996 | Bolle et al. | ..................... | 382/190 |
| 5,590,251 A * | 12/1996 | Takagi | ........................... | 345/604 |
| 5,771,311 A * | 6/1998 | Arai | ............................... | 382/162 |

(Continued)

FOREIGN PATENT DOCUMENTS
CA 2 403 855 9/2002
(Continued)

OTHER PUBLICATIONS

Takagi et al., Handbook of Image Analysis [Revised Edition], 2004, Tokyo University Press, pp. 192-201, 1187-1191, 1209, 1228-1229, 1519-1521, 1526-1528, 1534-1537, 1740-1743.

(Continued)

Primary Examiner — Kathleen Y Dulaney
(74) Attorney, Agent, or Firm — Knobbe Martens Olson & Bear LLP

(57) ABSTRACT

The method of identifying an effective pigment comprises:
a first step of imaging a target effective pigment to obtain image data thereof;
a second step of subjecting the obtained image data to background processing and extracting image data concerning a region containing one particle of the effective pigment as image data for processing;
a third step of extracting image characteristic parameters from the image data for processing; and
a fourth step of identifying the target effective pigment, based on the image characteristic parameters of the target effective pigment extracted in the third step, using a pre-prepared database that stores information on various kinds of effective pigments in such a manner as to correlate with the image characteristic parameters of various kinds of effective pigments extracted by conducting the second and third steps.

20 Claims, 13 Drawing Sheets

U.S. PATENT DOCUMENTS

| | | | |
|---|---|---|---|
| 6,411,953 B1* | 6/2002 | Ganapathy et al. | 1/1 |
| 6,507,824 B1* | 1/2003 | Yon et al. | 705/26.5 |
| 6,539,325 B1* | 3/2003 | Numata et al. | 702/127 |
| 6,628,829 B1* | 9/2003 | Chasen | 382/167 |
| 6,714,924 B1* | 3/2004 | McClanahan | 706/15 |
| 6,959,111 B2* | 10/2005 | Hirayama et al. | 382/167 |
| 7,035,464 B2* | 4/2006 | Masuda | 382/190 |
| 7,515,269 B1* | 4/2009 | Alexander et al. | 356/445 |
| 2001/0036309 A1* | 11/2001 | Hirayama et al. | 382/167 |
| 2002/0063721 A1* | 5/2002 | Masuda et al. | 345/600 |
| 2002/0164063 A1* | 11/2002 | Heckman | 382/133 |
| 2003/0048942 A1* | 3/2003 | Masuda | 382/165 |
| 2003/0216972 A1* | 11/2003 | Gotou et al. | 705/26 |
| 2003/0223060 A1* | 12/2003 | Graf et al. | 356/319 |
| 2004/0073526 A1* | 4/2004 | McClanahan | 706/15 |
| 2004/0179023 A1* | 9/2004 | Masuda et al. | 345/589 |
| 2004/0208352 A1* | 10/2004 | Neuberger et al. | 382/141 |
| 2004/0239968 A1* | 12/2004 | Gondek et al. | 358/1.9 |
| 2004/0252883 A1* | 12/2004 | Johansson et al. | 382/162 |
| 2005/0025357 A1* | 2/2005 | Landwehr et al. | 382/170 |
| 2005/0157346 A1* | 7/2005 | Kitagawara et al. | 358/2.1 |
| 2006/0034504 A1* | 2/2006 | Farina | 382/141 |
| 2006/0072805 A1* | 4/2006 | Tsipouras et al. | 382/134 |
| 2006/0210129 A1* | 9/2006 | Trendelenburg et al. | 382/128 |
| 2007/0126933 A1* | 6/2007 | Ting | 348/649 |

FOREIGN PATENT DOCUMENTS

| | | |
|---|---|---|
| CN | 1264823 | 8/2000 |
| CN | 1419672 | 5/2003 |
| EP | 1 128 282 A2 | 8/2001 |
| EP | 1 283 480 A1 | 2/2003 |
| GB | 2 340 931 A | 3/2000 |
| JP | 11-083848 A | 3/1999 |
| JP | 2001-265786 | 9/2001 |
| JP | 2002-140789 | 5/2002 |
| JP | 2005-065728 | 3/2005 |
| JP | 2006-244119 | 9/2006 |
| WO | WO 99/60353 | 11/1999 |

OTHER PUBLICATIONS

Office Action from Chinese Application No. 200710000775.9 dated Apr. 4, 2008.

European Search Report from Application No. EP 07 00 0796 dated May 7, 2007.

* cited by examiner

Fig.4
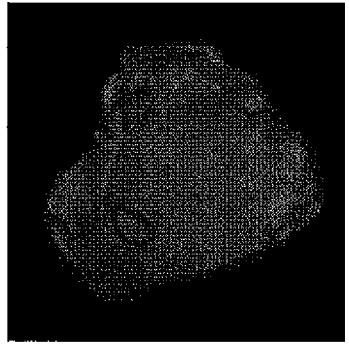
Example of an interference blue pigment particle
The background (black region) is not included in calculation.
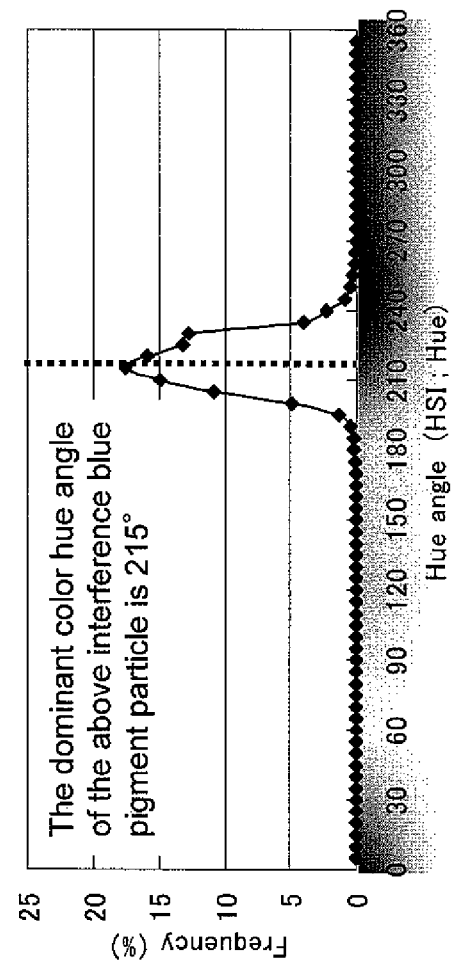
The dominant color hue angle of the above interference blue pigment particle is 215°
Hue angle histogram

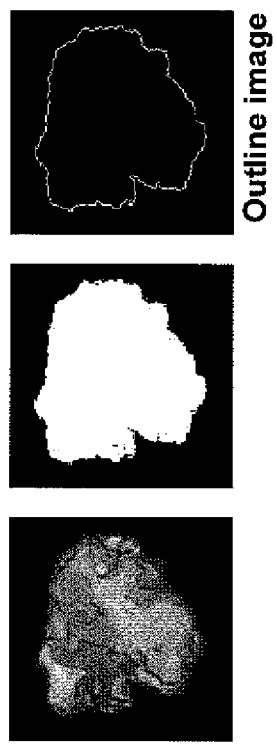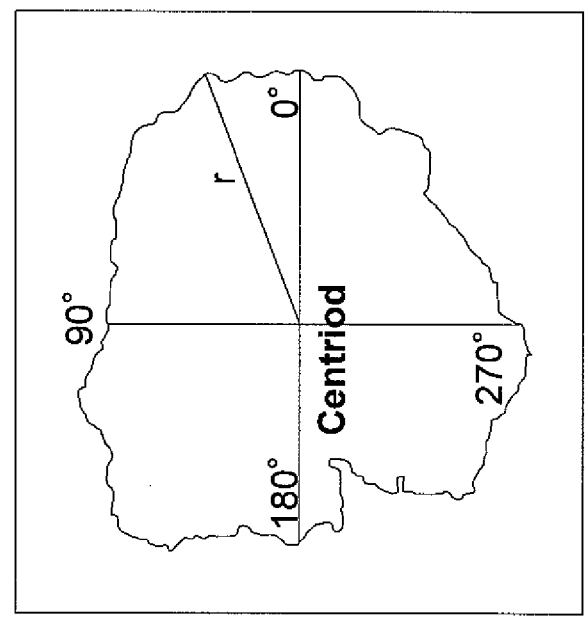
Fig. 6

Fig. 7A
Example of an interference green pigment particle
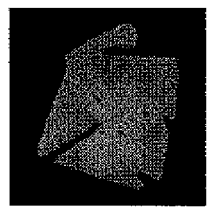
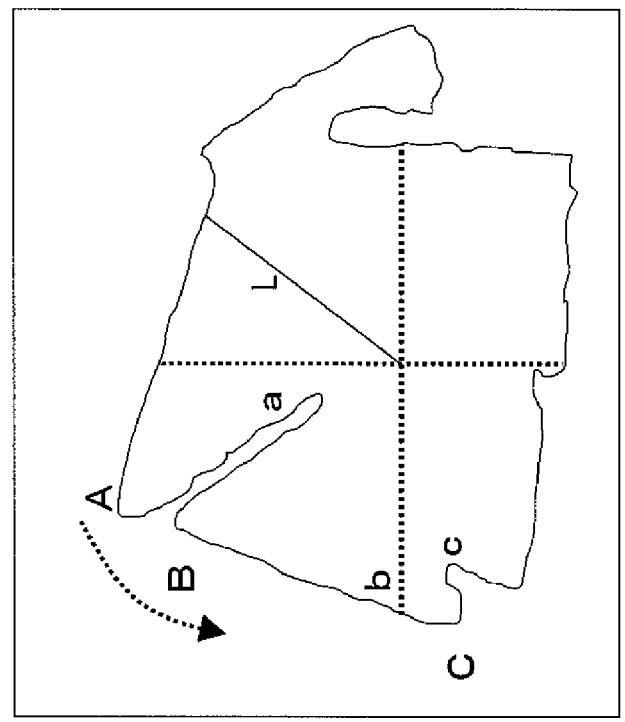

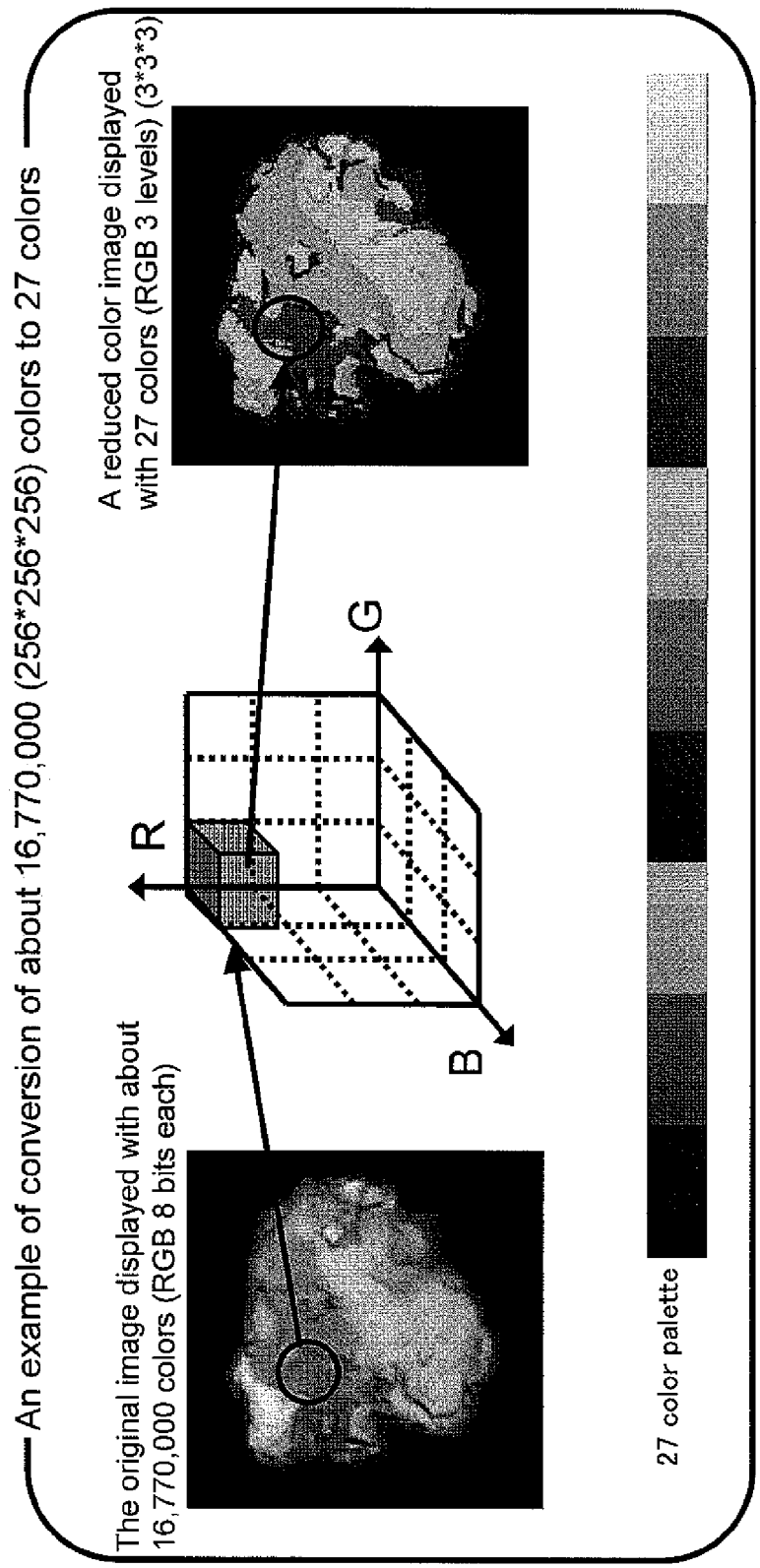
Fig. 8 Calculation of the number of particle constituent colors

Table. Correlation matrix of image characteristics parameters

| Variable name | sin-Cuh | cos-Cuh | Cus | r_ave | roundness | kosu | n_cut | colorCnt | filter_Iave | filter_Save |
|---|---|---|---|---|---|---|---|---|---|---|
| sin-Cuh | 1.00 | 0.39 | -0.21 | 0.13 | -0.14 | 0.03 | 0.03 | 0.36 | 0.29 | 0.02 |
| cos-Cuh | | 1.00 | -0.14 | 0.11 | -0.04 | 0.15 | 0.04 | -0.22 | -0.20 | -0.16 |
| Cus | | | 1.00 | 0.19 | -0.14 | 0.18 | 0.33 | -0.28 | -0.28 | 0.30 |
| r_ave | | | | 1.00 | 0.83 | 0.36 | 0.28 | 0.10 | -0.27 | -0.15 |
| roundness | | | | | 1.00 | -0.12 | -0.20 | -0.10 | 0.24 | 0.28 |
| kosu | | | | | | 1.00 | 0.06 | -0.02 | -0.13 | 0.18 |
| n_cut | | | | | | | 1.00 | -0.09 | -0.22 | 0.00 |
| colorCnt | | | | | | | | 1.00 | 0.67 | 0.41 |
| filter_Iave | | | | | | | | | 1.00 | 0.55 |
| filter_Save | | | | | | | | | | 1.00 |
| Variable name | sine of dominant color hue angle | cosine of dominant color hue angle | Saturation of the dominant color | Particle size | Particle circularity | Particle outline condition | Number of notches | Number of particle constituent colors | Intensity smoothness | Saturation smoothness |

Fig. 13

EFFECTIVE PIGMENT IDENTIFICATION METHOD, IDENTIFICATION SYSTEM, IDENTIFICATION PROGRAM, AND RECORDING MEDIUM THEREFOR

CROSS REFERENCE TO RELATED APPLICATION

This application claims the benefit and priority to Japanese Application Number 2006-12572. The disclosure of the above-described application is hereby incorporated by reference in its entirety.

BACKGROUND OF THE INVENTION (1) Field of the Invention

The present invention relates to a method of identifying a target effective pigment comprising preparing a database of image characteristic parameters of effective pigments of color layers in metallic/pearl coating or printing used to impart specific design effects; and an effective pigment identification system, an effective pigment identification program, and a recording medium therefor.

(2) Description of the Related Art

When an automotive outer panel is subjected to repair coating, the repaired portion needs to have the same color as the other portions of the panel. However, since the formula of the coating used at the time of car manufacturing are not publicly available, analysis of the coating formula may be necessary.

A computer color matching technique (hereinafter referred to as "CCM") comprising estimating a formula from data obtained by color measurements has been developed and used as a method for analyzing the formula of a coating whose composition is unknown.

CCM is a method for estimating color materials (color pigments, dyes) of a solid coating color (color whose appearance does not change with the angle of observation) from spectral reflectance data. This method uses Kubelka-Munk's two-flux theory, Duncan's color-mixing theory, and Saunderson's surface-reflectance correction theory in combination.

Japanese Unexamined Patent Publication No. 2001-265786 (hereinafter referred to as "Patent Document 1") discloses a method of identifying an effective material used in a coating color whose formula is unknown, the method comprising: visually extracting a characteristic parameter of the effective material used in a coating color whose formula is unknown; searching through an image database using the extracted characteristic parameter as a keyword; displaying on a monitor an image of a single effective material that most closely matches the parameter; and comparing the image of the coating color whose formula is unknown to the image of that single effective material.

However, no CCM method for coating colors containing effective pigments (e.g., aluminum flakes and like metal powders, mica flakes, plate-like iron oxide, etc.) has yet been developed for practical use for the following reasons. At the highlight portions which include the place where light's specular reflection occurs, the additive property of light beams (specularly reflected light, interference light) reflected from the effective pigment holds, and light absorption by color pigment(s) also occurs. In contrast, at the shadow portions which are not affected by specular reflection light, light absorption by effective pigment(s) and color pigment(s) mainly causes coloring. That is, it is impossible to generalize coloring characteristics of color materials of a coating containing effective pigment(s) over such a wide range as from highlight to shadow portions.

Therefore, a conventional method for identifying an effective pigment in a coating applied to an industrial product comprises observation by the naked eye or with a microscope and identification based on the observer's knowledge of characteristics of effective pigments. Therefore, experience and skill are required of the observer for correct identification, and the results depend on the observer's capabilities.

In recent years, new types of effective pigments have been developed and marketed one after another. Of flaky metallic pigments, for example, more than 100 kinds of aluminum flake pigments have been marketed which vary in production process, coloring technique, and particle size grade, and examples of metallic pigments include aluminum flakes whose surfaces are coated with an organic pigment, aluminum flakes whose surface have iron oxide deposited thereon by CVD, aluminum flakes produced by vapor deposition, aluminum flakes which have so-called silver dollar-type smooth surfaces, etc. Further, there are more than 300 kinds of effective pigments other than aluminum flakes. Therefore, it is almost impossible for the observer to memorize the characteristics of all the effective pigments.

In Patent Document 1, only the particle diameter and coloring characteristics of effective pigments are used as characteristic parameters. Therefore, although the method disclosed therein can crudely assess the type of effective pigment used, it cannot specify the brand of the effective pigment.

BRIEF SUMMARY OF THE INVENTION

The present inventors conducted research to solve the above problems of the prior art. Thus, an object of the present invention is to provide a method of identifying a target effective pigment, the method comprising preparing a database that correlates image characteristic parameters of effective pigments that impart specific design effects to industrial products with information on brands, etc. of the effective pigments, and searching through the database for matches using characteristic parameters extracted from an image of the target effective pigment. Other objects of the present invention are to provide an effective pigment identification system, an effective pigment identification program and a recording medium therefor.

To achieve the above objects, the effective pigment identification method (1) of the invention comprises:

a first step of imaging a target effective pigment to obtain image data thereof;

a second step of subjecting the obtained image data to background processing and extracting image data concerning a region containing one particle of the effective pigment as image data for processing;

a third step of extracting image characteristic parameters from the image data for processing; and a fourth step of identifying the target effective pigment, based on the image characteristic parameters of the target effective pigment extracted in the third step, using a pre-prepared database that stores information on various kinds of effective pigments in such a manner as to correlate with the image characteristic parameters of the various kinds of effective pigments extracted by conducting the second and third steps.

Effective pigment identification method (2) of the invention is the above method (1) in which the image characteristic parameters include characteristic parameters representing the color and surface condition of the effective pigment.

Effective pigment identification method (3) of the invention is the above method (2) in which the characteristic parameters representing the color of the effective pigment include sine and cosine values of the dominant color hue angle, and intensity and saturation of the dominant color, the dominant color hue angle being the mode of the hue angle histogram of the pixels in an image of one particle of the effective pigment in the HSI color space, the intensity of the dominant color being the average intensity of pixels having the dominant color hue angle, and the saturation of the dominant color being the average saturation of pixels having the dominant color hue angle.

Effective pigment identification method (4) of the invention is the above method (2) in which the characteristic parameters representing the surface condition of the effective pigment include the number of constituent colors, the average intensity gray level and the average saturation gray level, the number of constituent colors being the number of colors that occupy at least a certain proportion of a color-reduced image of one particle of the effective pigment, the average intensity gray level being determined by converting an image of one particle of the effective pigment into an intensity grayscale image, subjecting the grayscale image to edge extraction, and calculating the average intensity gray level of the pixels in the thus-obtained image; and the average saturation gray level being determined by converting an image of one particle of the effective pigment into a saturation grayscale image, subjecting the grayscale image to edge extraction, and calculating the average saturation gray level of the pixels in the thus-obtained image.

Effective pigment identification method (5) of the invention is any one of the above methods (2) to (4) in which the image characteristic parameters further include a characteristic parameter representing the particle shape of the effective pigment.

Effective pigment identification method (6) of the invention is the above method (5) in which the characteristic parameters representing the particle shape of the effective pigment include particle size, circularity, outline condition, and number of notches, the outline condition being the number of peaks and valleys in a two-dimensional outline profile obtained by plotting the distance from the centroid of one particle of the effective pigment in an image to the outline pixels in the order of tracing the outline, and the number of notches being the number of deep valleys in the two-dimensional outline profile.

Effective pigment identification method (7) of the invention is any one of the above methods (1) to (6) which comprises identifying the target effective pigment using a neural network using the image characteristic parameters as input units and information on the effective pigments as output units.

Effective pigment identification method (8) of the invention is the above method (7) in which the output values of the output unit are real numbers, and a predetermined number of effective pigments are selected from the database according to the output values of the output unit.

Effective pigment identification system (1) of the invention comprises:

an image-capturing device for imaging the target effective pigment and obtaining image data thereof;

a characteristic parameter detector for subjecting to background processing the image data input from the image-capturing device, extracting an image of one particle of the target effective pigment, then subjecting the extracted image of the one particle of the target effective pigment to image processing and computing various kinds of image characteristic parameters of the target effective pigment; and a recording device for storing a database that stores information on various types of effective pigments in such a manner as to correlate with image characteristic parameters calculated by the characteristic parameter detector;

the characteristic parameter detector identifying the target effective pigment, based on the image characteristic parameters calculated from the image of the target effective pigment input from the image-capturing device, using the database.

Effective pigment identification program (1) of the invention provides:

a first function of subjecting to background processing image data of a target effective pigment input to a computer and extracting image data of a region containing one particle of the effective pigment as image data for processing;

a second function of extracting image characteristic parameters from the image data for processing; and a third function of identifying the target effective pigment, based on the image characteristic parameters thereof extracted by the second function, using a pre-prepared database that stores information on various types of effective pigments in such a manner as to correlate with image characteristic parameters thereof extracted through the process by the first and second functions.

Computer readable recording medium (1) of the invention is for recording the effective pigment identification program (1).

According to the present invention, an unidentified effective pigment can be automatically and easily identified, based on image characteristic parameters thereof, using a pre-prepared database that stores brand information and image characteristic parameters of effective pigments.

Furthermore, when using a neural network technique, etc. for identification, a small number of most closely matching effective pigments can be selected as a result of automatic identification calculation, so that the operator can accurately and efficiently identify the unidentified effective pigment from the small number of the closely matching effective pigment candidates by comparing the images, and therefore higher identification accuracy can be achieved than with completely automatic identification.

Moreover, since the image characteristic parameters, such as the dominant color's hue, number of particle constituent colors, number of notches, etc., calculated from images of effective pigments, match human perception and enable a person to intuitively grasp the image of effective pigments, they are very useful as a reference to identify effective pigments that are similar.

The present invention enables identification of not only effective pigments themselves but also pigment dispersion pastes obtained by suspending effective pigments in solvents, effective pigment-containing coating compositions, metallic color coating films, films, printed matter, effective pigment-containing plastics, cosmetics, etc. Moreover, the present invention is useful for quality control of purchased effective pigments. Furthermore, it is applicable to criminal investigations because through analysis of coating fragments, one can identify the coating materials used, so that searches for automobiles having such coating materials applied thereon can be narrowed down.

BRIEF DESCRIPTION OF SEVERAL VIEWS OF THE DRAWINGS

FIG. 4 shows a hue angle histogram of an image of an interference blue pigment particle.

FIG. 6 shows the outline tracing, centroid, and particle size of one particle of an effective pigment in an image.

FIG. 7A shows the outline condition of an interference green pigment particle in an image.

FIG. 8 is a diagram illustrating the manner of calculating the number of colors constituting one particle in an image.

FIG. 13 shows the correlation coefficients of 10 kinds of image characteristic parameters obtained from 30 types of effective pigments (10 samples each) used in the Example of the present invention.

DETAILED DESCRIPTION OF THE INVENTION

The present invention is described below in detail with reference to the accompanying drawings.

The target effective material to be identified by the present invention refers to a pigment used to exhibit a metallic color. As described above, a "metallic color" refers to a color whose appearance changes with the angle of observation.

Examples of effective pigments include metal flakes such as aluminum, copper, nickel alloy, and stainless steel flakes; metal flakes whose surfaces are coated with metal oxide; metal flakes having a color pigment chemically adsorbed on or bonded to the surface; aluminum flakes having an aluminum oxide layer formed on the surface by an oxidation reaction; white mica and interference mica, the surfaces of which are coated with a metal oxide such as titanium dioxide; colored mica whose surfaces have a color pigment chemically absorbed thereon or are coated with a metal oxide such as iron oxide; reduced mica produced by reduction of an interference pigment; interference graphite whose surfaces are coated with a metal oxide such as titanium dioxide; silica flakes and alumina flakes whose surfaces are coated with a metal oxide such as titanium dioxide; plate-like iron oxide, glass flakes whose surfaces are coated with a metal or metal oxide; hologram pigments, cholesteric liquid crystal polymers, bismuth oxychloride pigments, etc.

Pigments to be identified by the present invention include effective pigments themselves, and pigment dispersion pastes obtained by suspending effective pigments in solvents, effective pigment-containing coating compositions, metallic color coating films, inks, films, printed matter, effective pigment-containing plastics, cosmetics, etc.

Figure 1:
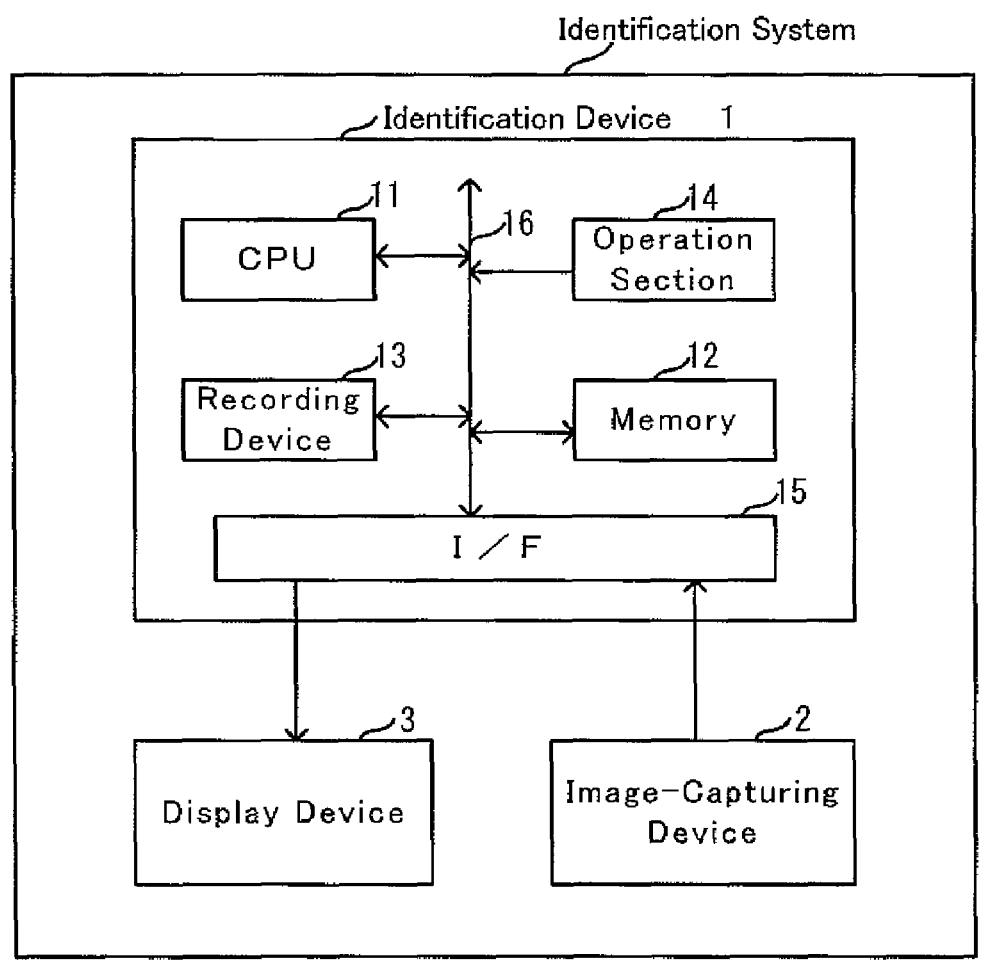
FIG. 1 is a block diagram schematically illustrating the structure of an effective pigment identification system according to one embodiment of the present invention.

FIG. 1 is a block diagram schematically illustrating the structure of an effective pigment identification system according to one embodiment of the present invention. The effective pigment identification system comprises an effective pigment identification device (hereinafter also referred to as "identification device") 1, an image-capturing device 2, and a display device 3. The effective pigment identification device 1 comprises: a CPU 11 for controlling each section included in the identification device 1 and executing the predetermined processing operations described later; a memory 12; a recording device 13 for storing a database which includes data that correlate image characteristic parameters of various kinds of effective pigments, such as color, particle diameter, etc., with information of their brands, etc.; an operation section 14 for receiving instructions from the outside; an interface 15 (hereinafter referred to as "I/F") that functions as an interface between the operation section 14 and an external device; and a data bus 16 for transmitting data between sections. The effective pigment identification device 1 receives image data from the image input device 2 via the I/F 15 and displays image data, etc. on the display device 3.

Examples of devices usable as the image input device 2 include microscopes, devices comprising an optical microscope and a digital camera connected thereto, video microscopes, etc.

The CPU 11 temporarily stores image data transmitted from the image input device 2 into memory 12, subjects the image to background processing by a method described below to extract an image of one particle of an effective pigment, then performs image processing to extract image characteristic parameters such as color, particle size, etc. and determines the most closely or exactly matching effective pigment(s) from a database recorded in the recording device 13, based on the extracted image characteristic parameters, using a neural network. The CPU 11 can execute various processing operations according to its own specific programming, or can execute a specific processing operation such as image processing according to a specific installed software.

The display device 3 is an image display device capable of displaying full color images. The CPU 11 can display the results of identification of an effective pigment on the display device 3 in a specified format via the I/F 15, or display information obtained in each processing step.

An effective pigment identification system according to one embodiment of the invention is briefly described below. First, an image of an effective pigment is captured using the image capturing device 2 and recorded in the memory 12. The recorded image is subjected to image processing to calculate image characteristic parameters. Subsequently, an effective pigment whose brand is known is selected as a candidate from a database, based on the calculated image characteristic parameters, using a neural network. Lastly, brand, lot number, etc. of the selected effective pigment are displayed on the display device 3.

First, preparation of a database is described below with reference to FIG. 2.

Figure 2:
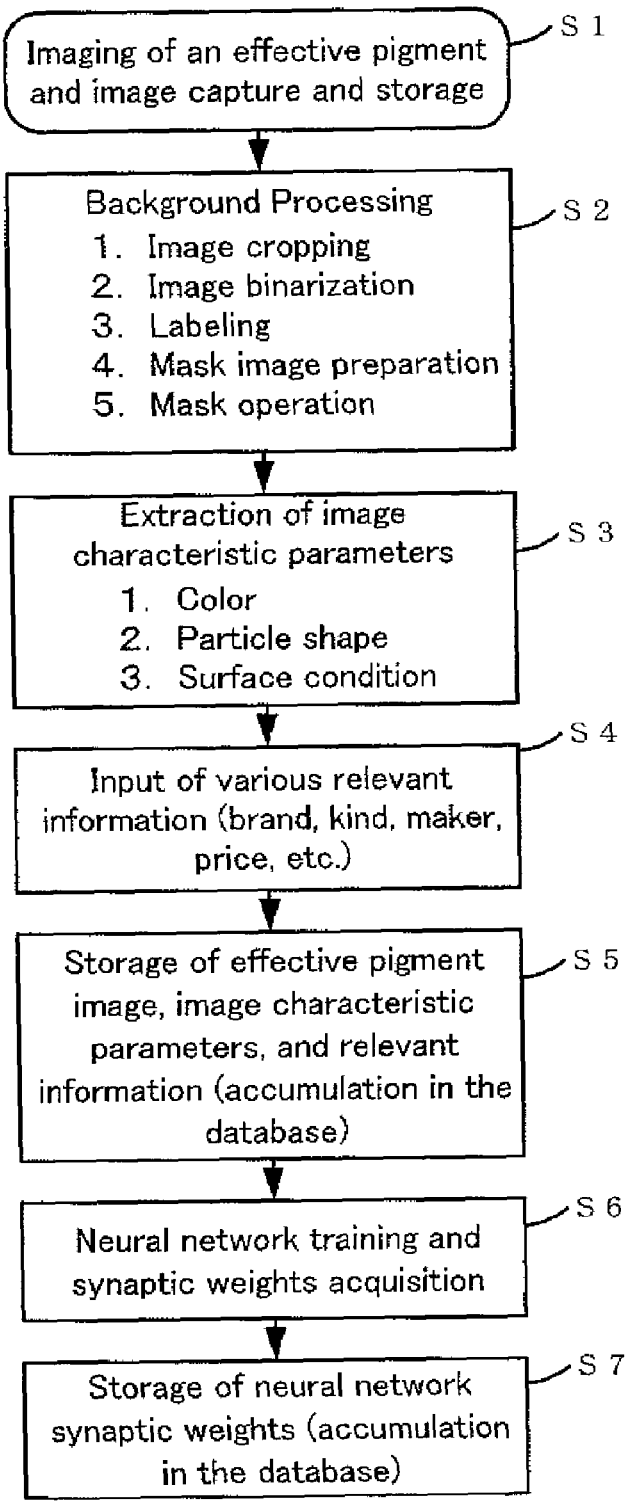
FIG. 2 is a flow chart showing steps of preparing a database.

FIG. 2 is a flowchart showing steps for preparing a database.

The processing operations described below are executed by CPU 11, unless otherwise specified.

As shown in FIG. 2, in the first step S1 for preparing a database, an effective pigment, more specifically, an effective pigment-containing coating film formed on the surface of a plate, etc. (hereinafter referred to as "coating film") is imaged by controlling an image-capturing device 2, and the obtained image data are stored in the memory 12 of the effective pigment identification device 1. To extract image characteristic parameters, it is desirable to take an image at a magnification of 100× to 3000× using a high magnification microscope as the image-capturing device 2. Although taking images at the same magnification is desirable in preparing the database, image magnification can be adjusted according to the type of effective material imaged because effective pigments do not necessarily have similar particle diameters. In this case, it is necessary to record both the used magnification and standard magnification images. From the viewpoint of accuracy, it is desirable that the observation magnification be adjusted in such a manner that the image data of one particle of an effective pigment has a size of at least 20×20 pixels. The illumination system used at the time of image capture is not particularly limited. However, since reflected light needs to be observed, known epi-illumination, reflected illumination, epi- and trans-illumination, and ring illumination are preferable.

When the coating film is not formed of a single effective pigment such as a metallic coating film, and more specifically, when imaging a coating film containing a plurality of effective pigments or color pigments, a portion less likely to be influenced by other effective pigments or coloring materials (e.g., color pigments) is imaged. More specifically, the operator can select with the naked eye an effective pigment in the surface layer of a metallic coating film, and take an image of it.

To prepare a database, it is desirable to apply a clear coating composition containing a single kind of effective pigment to a black substrate, dry and cure the composition, and take an image of the thus-obtained coating film. This is because when a coating composition is applied to a black substrate, it is less likely to be influenced by reflected light from the substrate and because if the clear coating composition does not have other coloring materials, it is free from absorption or diffusion of other coloring materials. Furthermore, with preparing several kinds of colored clear coating compositions by dispersing and mixing transparent pigments, dyes, etc. into a clear coating composition, it is also possible to apply likewise to a black substrate a coating composition prepared by mixing such a colored clear coating composition with one kind of effective pigment and image the thus-obtained coating film.

The image thus obtained is stored as image data in the memory 12 of the effective pigment identification device 1. The format of the stored image is not limited to an RGB bitmap format and may be a compressed data format, such as JPEG, without any particular limitation.

In the second step S2 for preparing a database, the image data stored in the memory 12 is subjected to background processing comprising cropping an image containing at least one complete particle of an effective pigment, image binarization, labeling, and mask operation. The background processing of the image data stored in the memory 12 is performed according to the following procedures by an operator who provides instructions to CPU 11 via the operation section 14, while observing an image on the display device 3 (see "Handbook of Image Analysis [Revised Edition]", Mikio Takagi, Haruhisa Shimoda (supervising editor), 1st edition, Tokyo University Press, Sep. 10, 2004; hereinafter referred to as "non-patent document 1").

Figure 3:
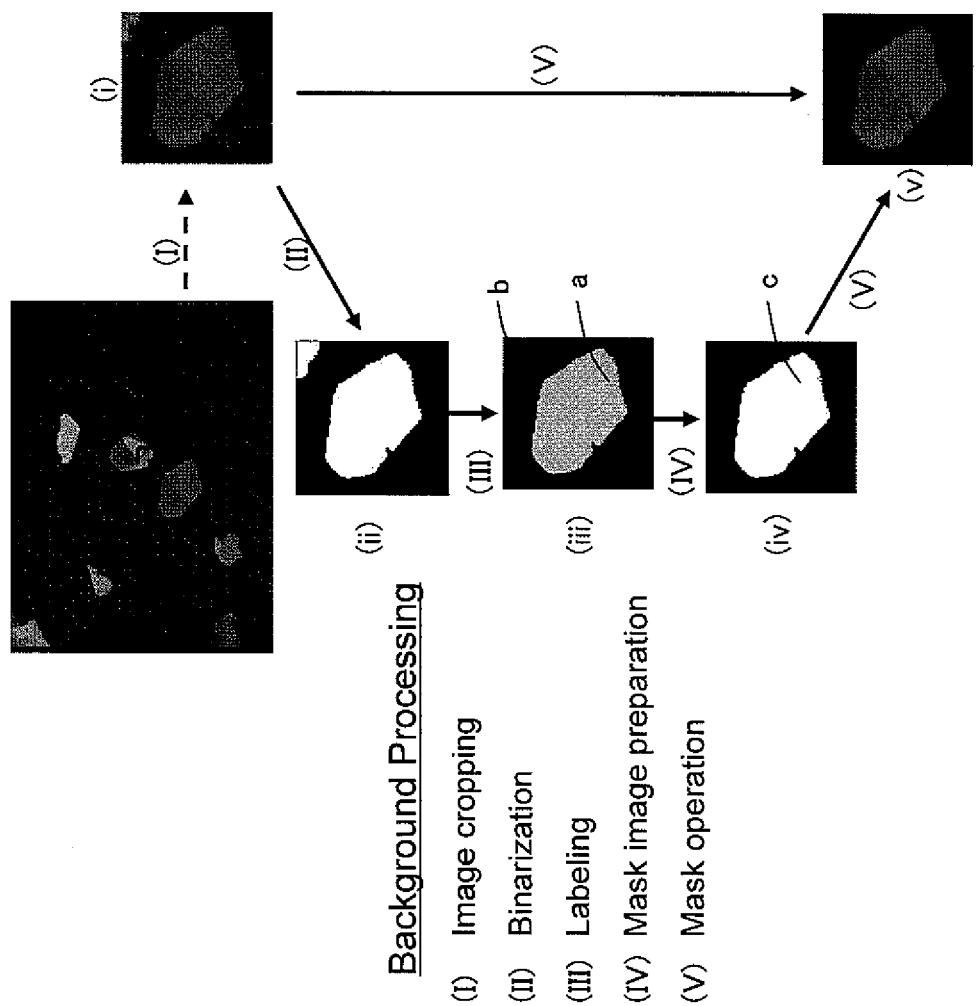
FIG. 3 is a diagram illustrating background processing of an image.

FIG. 3 is a diagram illustrating background processing of an image. Although grayscale images are shown in FIGS. 3, 4 and 6 to 9, they are in reality full color images.

As shown in FIG. 3, a region containing one target particle of the effective pigment is first cropped from the image taken in step S1 (I). For example, when using an image processing software, the region can be selected as a rectangular range. The operator decides the range to be cropped with the naked eye in such a manner that one sufficiently large effective image particle can be cropped.

Subsequently, binarization processing is performed on the cropped image (i) to specify the portion of the effective pigment particle, i.e., to clarify the location and outline of the effective pigment particle, so that the region to be extracted is output as white (for example, data 1), and the background as black (for example data 0) (II) (see the method described on page 1519 of non-patent document 1). The threshold for binarization processing is set while the operator observes the image on the display device 3. More specifically, for example, while comparing the unprocessed original image and the processed image which are displayed simultaneously, the operator manipulates the operation section 14 to determine a value, and then set the determined value as the threshold for binarization processing.

In the thus binarized image (ii), the effective pigment particle region is displayed as white. Since the number of such white regions (groups of contiguous white pixels) is usually more than one, labeling is performed in such a manner that each white region receives a different label (III) (see the method described on page 1526 of non-patent document 1). A labeled image is shown in (iii). Two block portions, a and b, are present in (iii) and are given different labels and displayed with different colors. After labeling, the white region that occupies the largest area in the image (a in FIG. 3) is selected and specified as the region of one effective pigment particle. When a white region has a hole, labeling is performed after padding.

A mask image (iv) is prepared by applying a background color (black) to all the portions other than the above specified one effective pigment particle region (IV), and the original image (i) is combined with the specified one effective pigment particle region to make a composite image (V) (see page 1740 of non-patent document 1), i.e., so-called mask operation is performed, thereby obtaining an image (v) in which only the one effective pigment particle region is fully colored and elsewhere (background) has an intensity level of zero. The thus background-processed image is stored in the database of the recording device 13 in such a manner as to correlate with the brand of the effective pigment.

In the third step S3 for preparing a database, image characteristic parameters of the background-processed image are extracted.

The image characteristic parameters of effective pigments to be extracted in the present invention can be classified into three types: parameters indicating colors, parameters indicating particle shapes, and parameters indicating surface conditions, which are described below in detail. The features of each type of image characteristic parameters and how to determine the parameters are described below.

(Color)

Color is important when characterizing effective pigments. Three color attributes (hue, intensity, saturation) can be used as image characteristic parameters. When a two-dimensional image of an effective material is taken, one effective pigment particle region (for example, c of FIG. 3) may have different colors, pixel by pixel. Therefore, the dominant color of the pixels in the region is determined, and saturation, intensity and hue of the dominant color can be used as image characteristic parameters.

According to one embodiment of the present invention, the dominant color is determined in the following manner. First, all the pixels of the effective pigment particle region in an image are converted from RGB data, i.e., the color system used in computers, etc. to HSI (hue, saturation and intensity) data, i.e., a color system closely matching human perception (see page 1187 of non-patent document 1). The method of transformation from RGB color system to HSI color system data is not particularly limited. In one embodiment of the present invention, a hexagonal pyramid color model is used. Subsequently, as shown in FIG. 4, a hue histogram that shows hue distribution of pixels is obtained and the mode is used as the dominant color hue. Furthermore, the average saturation of the pixels having the dominant color hue is determined and used as the saturation of the dominant color.

Figure 5:
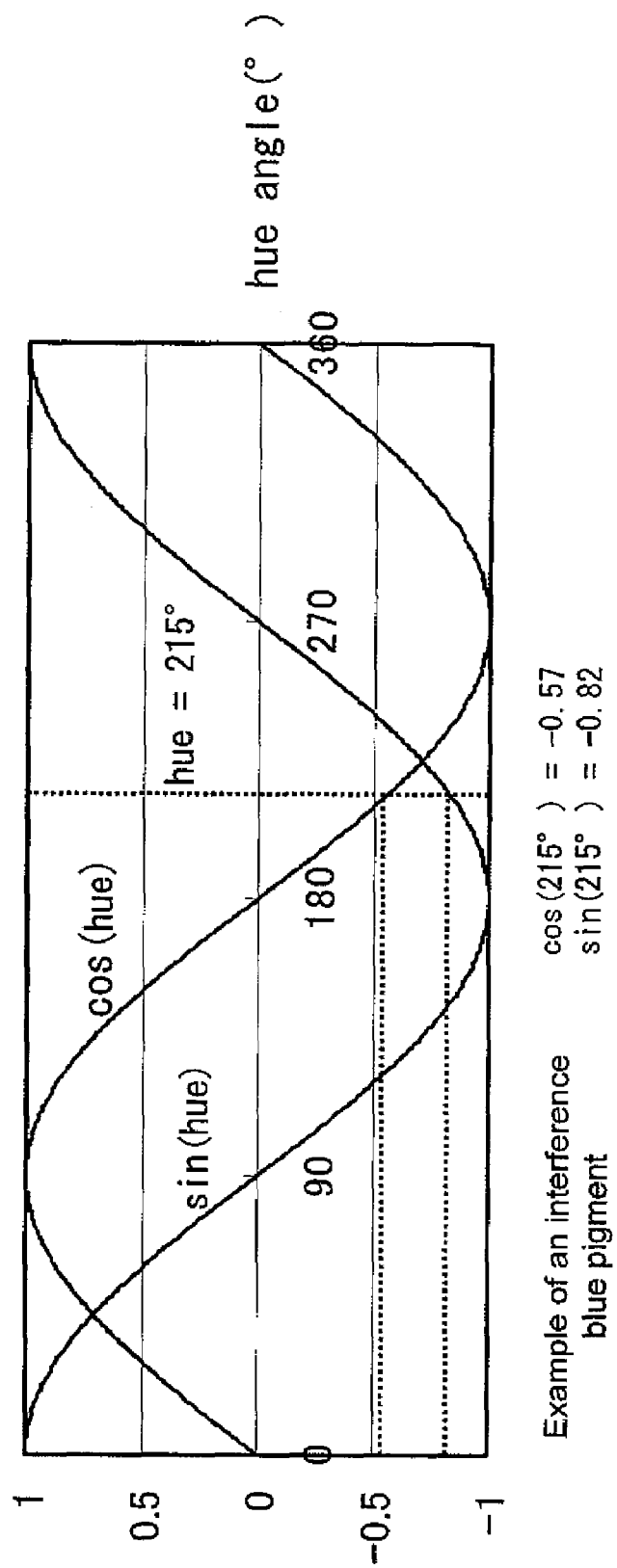
FIG. 5 shows hue angle sine and cosine values.

Since the hue is expressed as an angle (a non-negative integer from 0 to 359°) in the HSI data obtained by conversion using the hexagonal pyramid color model, it is discontinuous from 359° to 0°, which impedes statistical calculation described later. Therefore, according to one embodiment of the present invention, hue angle sine and cosine values as shown in FIG. 5 are determined and used independently as image characteristic parameters. FIG. 5 shows an example of an interference blue pigment particle. The hue angle is 215°, and image characteristic parameters are cos (215°)=−0.57 and sin (215°)=−0.82.

Further, in addition to such saturation and hue angle sine and cosine values, intensity can also be used as an image characteristic parameter. As with saturation, the average intensity of the pixels having the dominant color hue is determined and used as the intensity of the dominant color.

(Particle Shape)

As with color, particle shape is also important when characterizing effective pigments. The image characteristic parameter representing particle shape can be selected from particle size, representing particle dimensions; circularity, representing roundness; outline condition, representing outline smoothness, and number of notches, representing the presence of deep nicks. Such image characteristic parameters representing particle shape can be determined in the following manner.

First, as shown in FIG. 6, the outline of one effective pigment particle in the background-processed image obtained in step S2 is traced and the pixels corresponding to the outline (hereinafter referred to as "outline pixels") are determined. Next, the centroid of the one effective pigment particle is determined. Subsequently, the distance from the centroid pixel to each of all the outline pixels is determined and the average is calculated, i.e., the average distance from the centroid to the outline is calculated, and a dimension equivalent to radius is used as the particle size r. The particle size r is calculated by the following formula:

$$r = \left( \sum_{i=1,n} \sqrt{(x_i - a)^2 + (y_i - b)^2} \right) \Big/ n \qquad \text{[Formula 1]}$$

wherein (a, b) are coordinates of the centroid, $(x_i, y_i)$ are outline pixel coordinates, and n is the number of outline pixels.

Further, the outline length of one effective pigment particle in the image is calculated by outline processing, and the circularity is calculated from the outline length and the above calculated particle size r (see page 1534 of non-patent document 1). More specifically, the circumference is calculated from the above calculated particle size r equivalent to radius, and the ratio between the circumferential length to the outline length is used as the circularity, representing particle image's roundness.

Figure 7B:
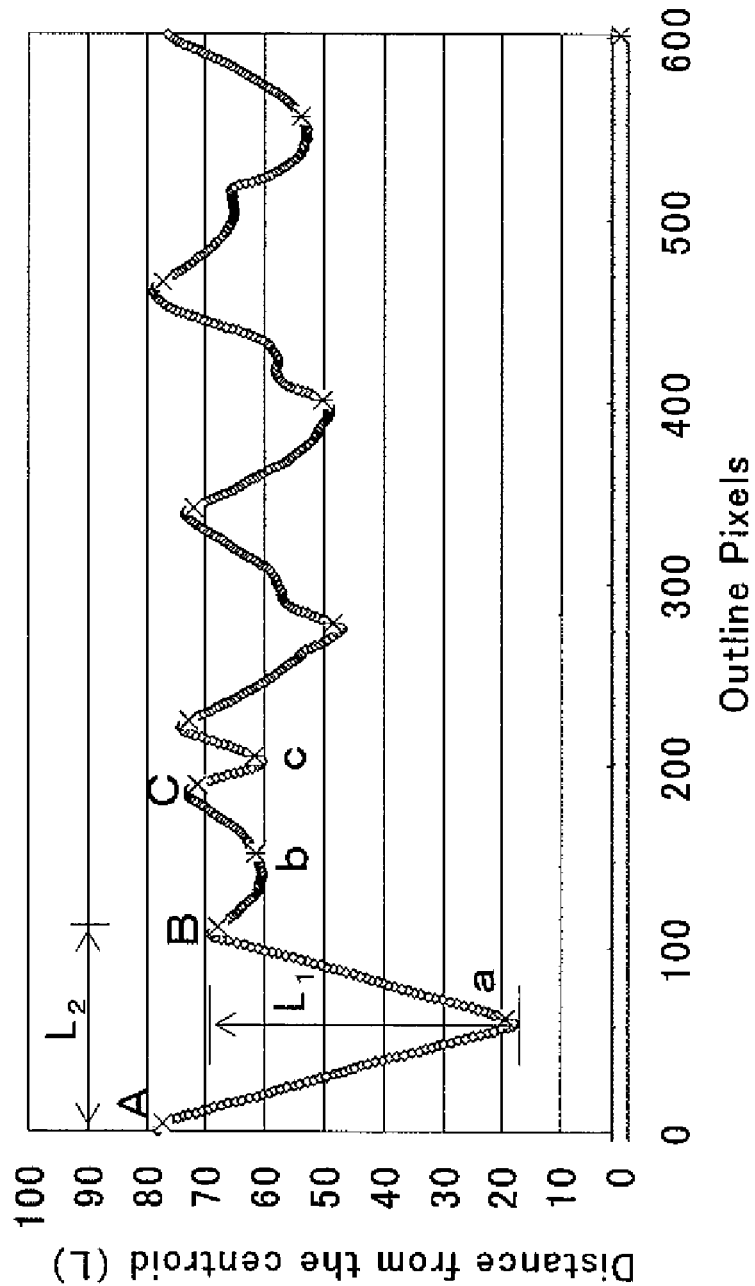
FIG. 7B shows the outline profile of the interference green pigment particle in the image shown in FIG. 7A.

Subsequently, as shown in FIGS. 7A and 7B, a two-dimensional graph of the outline profile of the distance L from the centroid of the particle image to the outline thereof, i.e., to each contour pixel (FIG. 7B) is prepared, and maximum and minimum points of the distance L in the outline profile are sought out to determine the peaks and valleys (see Japanese Unexamined Patent Publication No. 2006-244119). The number of peaks and valleys of the outline profile is used as an index representing outline smoothness (contour condition). In FIG. 7B, the outline pixel sequence traced from a certain outline pixel along the outline is plotted as the abscissa (more specifically, the pixels are aligned counterclockwise from the point A in FIG. 7A). The distance L from the centroid of the particle image to each contour pixel is plotted as the ordinate. In FIGS. 7A and 7B, A, B and C represent peaks, and a, b and c represent valleys.

Further, when an extremely deep valley exists in the outline profile, i.e., when the effective pigment has a local deep depression or nick, it is defined as a notch. The number of notches is counted according to predetermined criteria, for example, criteria that the distance difference $L_1$ between an adjacent peak and valley from the centroid is at least 40 pixels, and the distance $L_2$ between adjacent peaks is 40 pixels or less. The number of notches is also used as an image characteristic parameter. For example, in FIGS. 7A and 7B, "a" represents a notch.

(Surface Condition of the Effective Pigment)

The surface condition is also important when characterizing effective pigments. In two-dimensional images, the surface condition is represented by intensity level variation and thus can be monitored indirectly. More specifically, the surface condition of effective pigment particles can be represented by two factors, i.e., particle constituent colors and particle surface irregularity. In particular, optical images vary in intensity and saturation due to the nature of the substrate of the effective pigment, production process-derived surface irregularities and coating layer thickness differences. Therefore, according to one embodiment of the present invention, the surface condition may be indirectly represented by calculating the number of colors in the image of one effective pigment particle (particle constituent colors) and color heterogeneity (particle smoothness) due to color intensity variation in the HSI data.

First, "number of particle constituent colors" representing the surface condition, i.e., the number of colors in an image of one effective pigment particle, is determined according to the following procedure and used as an image characteristic parameter. More specifically, as shown in FIG. 8, full-color image data are subjected to color reduction processing by uniform quantification (see page 1209 of non-patent document 1), and the color that occupies at least 1.0% of the obtained image, for example, a 27-color image, is regarded as a particle constituent color, and the total number of such colors is determined and used as the number of particle constituent colors. FIG. 8 shows an example thereof.

Figure 9:
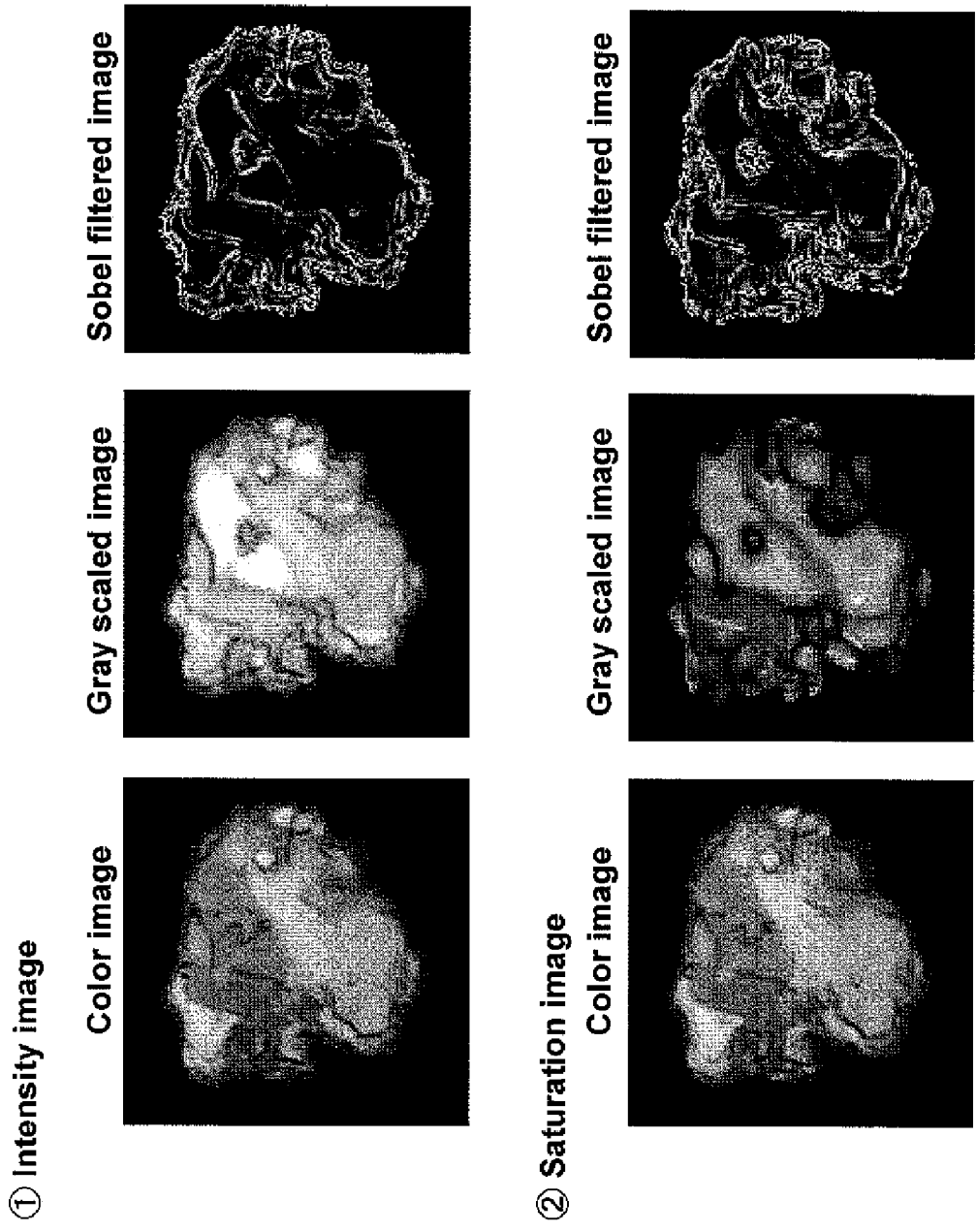
FIG. 9 shows preparation of grayscale images and edge extraction thereof.

With respect to "particle smoothness" representing the surface condition, when there are differences in the intensity and saturation of the particle surface in the obtained image, humans can perceive surface irregularities. Therefore, in one embodiment of the present invention, an image characteristic parameter is extracted by focusing on image regions where the intensity levels change. More specifically, as shown in FIG. 9, using an image of one effective pigment particle, an HSI-intensity grayscale image is prepared and then subjected to edge extraction processing or filtering (see page 1229 of non-patent document 1). The average gray level of the obtained image is determined as a characteristic parameter representing the surface intensity smoothness, i.e., "average intensity gray level". Likewise, a saturation grayscale image is prepared from the original image and subjected to edge extraction processing, and the average gray level of the obtained image is determined as an image characteristic parameter representing the surface saturation smoothness, i.e., "average saturation gray level".

When pixel values (gray levels) of the edge-extracted image are $g_1, g_2, \ldots, g_n$, the average gray level G is calculated by the following formula:

$$G = \Sigma g_i/n \quad \text{[Formula 2]}$$

wherein i is 1, 2, ... n.

The edge extraction processing method is not particularly limited, and known methods, for example, primary differentiation such as Sobel filtering may be used.

Thus, a total of 11 kinds of image characteristic parameters, i.e., four color-related image characteristic parameters including sine and cosine values of dominant color hue angle, dominant color saturation, and dominant color intensity; four particle-shape-related image characteristic parameters including particle size, circularity, outline condition, and number of notches; and three surface condition-related image characteristic parameters including number of particle constituent colors, average intensity gray level, and average saturation gray level, can be extracted from an effective pigment.

To prepare a database, extraction of each of the above image characteristic parameters for one effective pigment particle image is made at least once per kind of effective pigment, and preferably at least 10 times.

In the fourth step S4 for preparing a database, input of the brand, lot number, manufacturer, and various other data (particle size, specific surface area, surface treatment, etc.), type (raw material, coloring, etc.), price, etc. is received, for example, via the operation section 14, and stored in the memory 12.

In the fifth step S5 for preparing a database, the image characteristic parameters extracted from the image in step S3 are stored in the recording device 13 in such a manner that the image characteristic parameters correlate with brands, etc. of the effective pigments acquired in step S4. It is also possible to store information other than image characteristic parameters, such as the images themselves obtained in each image processing step, in such a manner as to enable correlation. The data correlation and storage can be done by known methods.

The method of specifying the brand of an unidentified effective pigment using the thus-obtained database may be any of various methods such as statistical calculation, neural network, etc. In one embodiment of the present invention, an identification method using a hierarchically structured network using the above-mentioned image characteristic parameters as input information and the brand (or kind) of effective pigment as output information is used, and described later in detail (see page 193 of the non-patent document 1).

Therefore, in the sixth step (step S6) for preparing a database, a neural network is constructed, and back-propagation training is performed using as training data data correlating image characteristic parameters with brands stored in the database to obtain the synaptic weights, etc.

More specifically, a neural network is prepared using the kinds (number) of image characteristic parameters as the number of input units and the kinds or brands (number) of effective pigments as the number of output units. Not all the characteristic parameters extracted above have to be used as input unit image characteristic parameters. Although a characteristic parameter relating to color is essential, other characteristic parameters are optional. When an image characteristic parameter representing particle shape is included, identification accuracy increases. When an image characteristic parameter representing surface condition is also included, identification accuracy is further enhanced.

Figure 10:
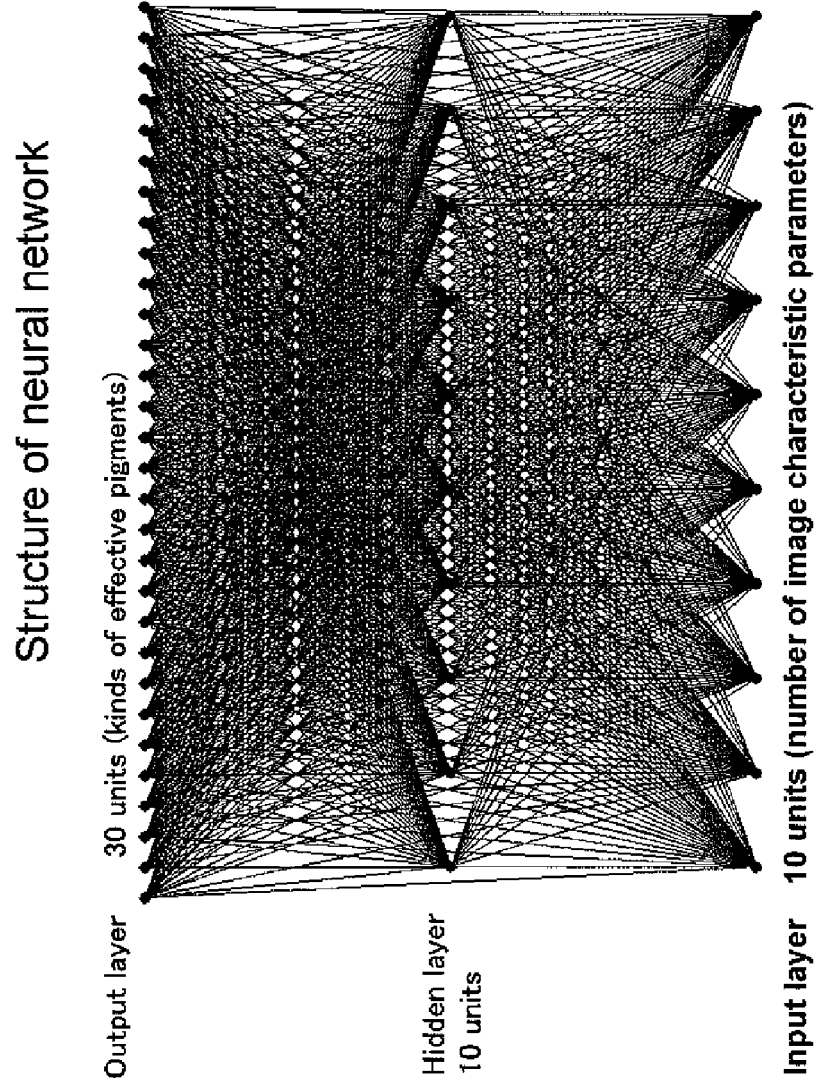
FIG. 10 illustrates the structure of a neural network.

FIG. 10 illustrates the structure of a neural network. In the figure, 10 kinds of normalized image characteristic parameters other than the dominant color intensity are used as input units for the input layer; brands of 30 kinds of effective pigments are used as output units of the output layer; and 10 units are provided in a hidden layer. Normalization of each image characteristic parameter can be performed, for example, using the following formula:

$$X_{i,j} = (P_{i,j} - P_{min,i})/(P_{max,i} - P_{min,i})$$

wherein i represents the kind of characteristic parameter, $X_{i,j}$ represents the normalized value of the characteristic parameter i obtained from an image j, $P_{i,j}$ represents the value of the characteristic parameter i obtained from the image j, $P_{max,i}$ is the maximum value of the characteristic parameter i in the training data, and $P_{min,i}$ is the minimum value of the characteristic parameter i in the training data.

Herein, although data that correlate the normalized image characteristic parameter with the effective pigment brand are used as training data (teaching data), image characteristic parameters preferably used as training data are those obtained by preparing at least 10 images per kind of effective pigment and excluding therefrom those having a strong cross-correlation in order to enhance identification accuracy. Although the training is preferably performed at least 10 million times, the number of training events can be adjusted according to the image characteristic parameter used, effective pigment brand, training data, etc., while checking convergence condition.

In the seventh step S7 for preparing a database, the neural network synaptic weights thus obtained by training are stored in the recording device 13, together with neural network constituent information (the number of layers, number of units, etc.), normalized image characteristic parameters, and the maximum and minimum values of each characteristic parameter.

A method of identifying an effective pigment according to one embodiment of the present invention is described below with reference to the flow chart of FIG. 11, using the identification system shown in FIG. 1.

The method of identifying an effective pigment contained in a metallic/pearl coating color material to impart design effects is described below. The processing operations described below are executed by CPU 11, unless otherwise specified.

Figure 11:
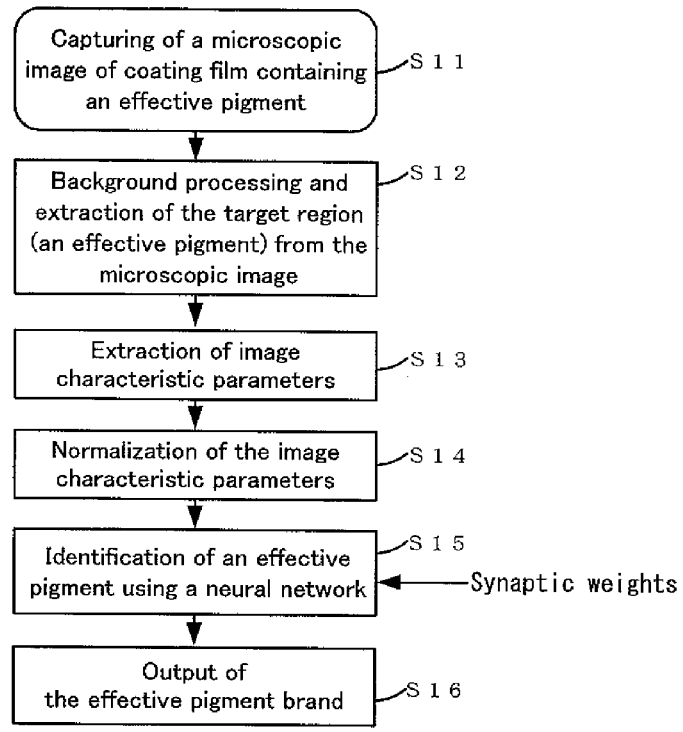
FIG. 11 is a flow chart illustrating a method of identifying an effective pigment according to one embodiment of the present invention.

First, in step S11 shown in FIG. 11, as with database preparation, an image input device 2, for example, a microscope, is used to image a coating film containing an effective pigment. The obtained image data are recorded via the I/F 15 in the memory 12 as, for example, a full-color JPEG image. Care should be taken that when the coating film contains two or more kinds of effective pigments, the observer should make careful observation with the microscope to select only the target effective pigment particle.

Subsequently, in step S12, as with data preparation, the single target effective pigment particle to be identified is cropped from the full-color image recorded in step S11 under appropriate instructions to CPU 11 via the operation section 14, and background processing steps, including image binarization, labeling, and background processing, are performed to prepare background-processed image data of one effective pigment particle.

In step S13, as with database preparation, a plurality of image characteristic parameters representing color, particle shape, and surface condition are extracted from the background-processed effective pigment particle image obtained in step S12 under instructions to CPU 11 via the operation section 14.

In step S14, the maximum and minimum values of each kind of image characteristic parameter are retrieved from the database stored in the recording device 13, and the values of each kind of image characteristic parameter obtained in step S13 are normalized.

In step S15, the effective pigment brand is identified based on the extracted image characteristic parameters. Various statistical methods can be used as the identification method. According to one embodiment of the present invention, the brand is identified by using a neural network in which the above normalized image characteristic parameters are used as input information and the effective pigment brand as output information, and synaptic weights are predetermined using a back-propagation algorithm (see page 201 of the non-patent document 1). Therefore, the normalized image characteristic parameters obtained in step S14 are input to the neural network input units, and the effective pigment is identified by the neural network using the neural network synaptic weights in the database stored in the recording device 13.

In step S16, information on the brand, etc. of the effective pigment identified by the neural network is output to the display device 3 via I/F 15.

Thus, the effective pigment identification system of the present invention extracts image characteristic parameters from an image of an unidentified effective pigment and automatically and easily identifies the brand of the unidentified effective pigment using a neural network, based on extracted image characteristic parameters, using a database prepared beforehand using image characteristic parameters of known effective pigments.

Although a method of identifying an effective pigment (metallic/pearl coating color) in the coating film is described above, the identification method of the present invention is not limited to such an application and is also applicable to effective pigment-containing films, plastics, etc. cosmetics, effective pigments themselves, etc.

Depending on the database-registered data on effective pigments, it may also be possible to perform identification using only some of the identification data in the database and/or to limit or extend the range of neural network output data. More specifically, when the type of unidentified pigment is roughly known, limiting the range of the identification data in the database to the expected range may be effective. Instead of binary evaluation with outputs such as "yes" or "no" ("1" or "0"), it is also possible for the neural network to output real numbers in the range from 0 to 1 and sort the output values in descending order from the highest to the lowest and select as candidates a predetermined number of brands of effective pigments that are of similarity.

For example, when new synaptic weights are obtained by retraining the neural network using as output units types of roughly known effective pigments, the brand of an unidentified effective pigment can be identified using the new synaptic weights, thereby enhancing the identification accuracy.

When the kind of effective pigment cannot be identified by a "yes/no" format, it is also possible to output data as real numbers in the range from 0 to 1 from the neural network and to present, for example, the 5 most highly ranked effective pigments as effective pigments similar to the unidentified effective pigment.

When an unidentified effective pigment is identified by the identification method of the present invention and the obtained result is not the correct answer as the observer knows it to be, sample data, in particular, data of samples that have not been recognized correctly, may be added to the database and retraining of the neural network can be performed to obtain the correct answer. The retaining can provide new synaptic weights and samples that have not been recognized correctly can be identified with greater accuracy. More specifically, more accurate identification can be made by adding correct sample data to database.

EXAMPLES

Figure 12:
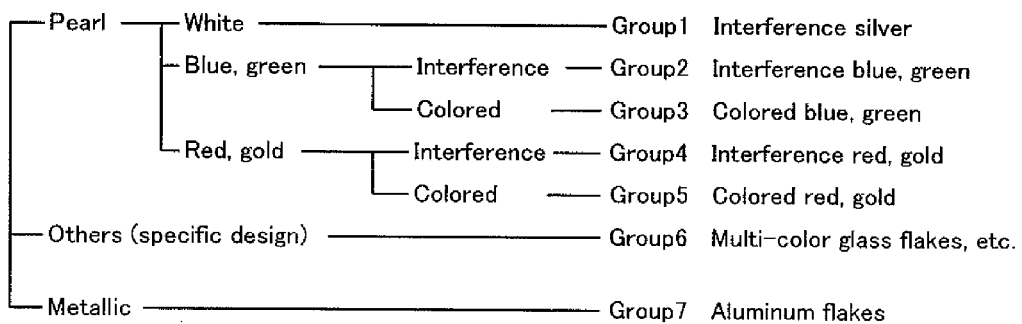
FIG. 12 is a diagram showing classification of effective pigments used in the Examples of the present invention.

Examples are given below to illustrate the invention in more detail.
(1) Preparation of Effective Pigments Effective pigments were roughly classified as shown in FIG. 12, and 30 kinds of brands that differ in coloring, particle size, and surface condition were selected from the groups. More specifically, 30 kinds were selected from aluminum flake pigments (brands that differ in particle size), colored aluminum flake pigments (blue, green, red), colored pearl pigments (red), interference pearl pigments (brands whose interference color is red, gold, yellow, green, blue, or purple, whose substrate is natural mica or alumina flakes, and which are different in particle size), silver pearl pigments (brands which are different in substrate and particle size), and multicolored pigments.
(2) Preparation of Effective Pigment-containing Coating Films Each effective pigment selected in (1) was added to a respective nitrocellulose clear coating composition ("ACRIC 2026GL", product of Kansai Paint Co., Ltd.) in a proportion of 1 part by mass of effective pigment on a solids basis per 100 parts by mass of resin solids of the clear coating composition, and mixed with stirring. The resulting coating composition was diluted to adjust the viscosity to be suitable for coating. The thus-adjusted coating composition was applied using a bar coater No. 20 to art paper pre-coated with black to form a coating film with a thickness of about 15 μm when dried.
(3) Imaging Effective Pigments Using a video microscope as an image-capturing device, each coating film thus prepared was imaged at a magnification of 2500× using an epi-illumination system. The obtained image data were stored in the memory of the identification device (computer).

Ten image data sets of each kind of effective pigment were obtained. Thus the total of 30×10=300 images were obtained.
(4) Image Background Processing, Characteristic Parameter Extraction, and Normalization As with database preparation as described above, the stored image was processed using an identification device, and 10 sets of image characteristic parameters per kind of effective pigment (10 kinds of characteristic parameters other than dominant color intensity) were extracted. Subsequently, 30×10=300 samples of each kind of extracted image characteristic parameters were independently normalized.
(5) Examination of Characteristic Parameter Correlation A correlation matrix was calculated for the 10 types of image characteristic parameters, each has 300 samples, respectively. FIG. 13 shows the obtained correlation coefficients. All the cross-correlation coefficients were less than 0.9, thus confirming that correlations between different characteristic parameters are low. Therefore, these characteristic parameters are considered to be appropriate.
(6) Database Preparation Data correlating the normalized image characteristic parameters obtained in (4) above with brands of effective pigments, images of single effective pigment particles, and the maximum and minimum values of each kind of image characteristic parameters were stored as database in the memory of the identification device.
(7) Neural Network Learning For identification using a neural network, back-propagation training was performed using data correlating the normalized image characteristic parameters with effective pigment brands as training data. Synaptic weights of the neural network obtained by training were also stored in the database. As shown in FIG. 10, the structure of the neural network has 10 input units, 30 output units, a hidden layer, 10 hidden layer units, and a bias input unit. The function used was a sigmoidal function; the number of training events was 10 million; the training ratio was 0.8; and the allowable error was 0.1.

(8) Effective Pigment Image Acquisition to Evaluate Identification Accuracy

To evaluate the accuracy of the identification method, two more images of each kind of effective pigments were captured in the same manner as the images obtained in (1) to (3) above, obtaining a total of 2×30=60 images.

(9) Image Background Processing, Characteristic Parameter Extraction, and Normalization After background processing was performed on each of the above 60 images, image characteristic parameters were extracted. The obtained image characteristic parameters were normalized using the corresponding maximum and minimum values of each characteristic parameter stored in the database in (6).

(10) Effective Pigment Identification

Effective pigments were identified based on the normalized image characteristic parameters obtained in (9) above, using the neural network prepared in (7) above. As a result, the probability of accurately identifying the effective pigment brand was found to be 74.1%, and the probability that the correct brand is included in the five brands selected as candidates for the correct effective pigment was 94.8%. Thus, since the effective pigments were identified with very high accuracy, the used image characteristic parameters are considered to be highly effective.

The above embodiment and examples are given to illustrate the present invention, but the invention is not limited thereto. Various modifications may be made to the effective pigment identification device and identification system of the invention without departing from the spirit and scope of the invention. Likewise, various modifications may be made with respect to the effective pigment identification method and program of the present invention without departing from the spirit and scope of the invention.

What is claimed is:

1. A method of identifying an effective pigment comprising:
   imaging the effective pigment to obtain first image data, wherein the imaged effective pigment imparts a design effect that changes appearance with angle of observation;
   subjecting, using a computer, the obtained image data to background processing and extracting image data concerning a region containing only one particle of the effective pigment as second image data;
   calculating, using the computer, characteristic parameters of the effective pigment from the second image data; and
   identifying the effective pigment based at least in part on the extracted characteristic parameters and a pre-prepared database that stores, in a memory, information indicative of various kinds of effective pigments respectively associated with image data and characteristic parameters of the various kinds of effective pigments,
   wherein the identified effective pigment imparts a design effect that changes appearance with angle of observation and the various kinds of effective pigments stored in the database each impart a design effect that changes appearance with angle of observation, and
   wherein the stored image data of the various kinds of effective pigments each contain only one particle and the characteristic parameters of the various kinds of effective pigments are obtained by conducting said subjecting and said calculating, the characteristic parameters including parameters representing a color of the effective pigment, the parameters representing; the color of the effective pigment including sine and cosine values of a dominant color hue angle, intensity of the dominant color, and saturation of the dominant color.

2. The method according to claim 1 wherein the characteristic parameters further include at least one characteristic parameter representing a surface condition of the effective pigment.

3. The method according to claim 2 wherein the characteristic parameters representing the surface condition of the effective pigment include a number of constituent colors, an average intensity gray level, and an average saturation gray level,
   the number of constituent colors being a number of colors that occupy at least a certain proportion of a color-reduced image obtained by color-reducing an image of one particle of the effective pigment,
   the average intensity gray level being determined by converting an image of one particle of the effective pigment into an intensity grayscale image, subjecting the intensity grayscale image to edge extraction to obtain an edge image, and calculating the average intensity gray level of the pixels in the intensity edge image; and
   the saturation gray level average being determined by converting an image of one particle of the effective pigment into a saturation grayscale image, subjecting the saturation grayscale image to edge extraction to obtain an edge image, and calculating the average saturation gray level of the pixels in the saturation edge image.

4. The method according to claim 3 wherein the characteristic parameters comprise at least one characteristic parameter representing a particle shape of the effective pigment.

5. The method according to claim 2 wherein the image characteristic parameters further include at least one characteristic parameter representing a particle shape of the effective pigment.

6. The method according to claim 5 wherein the characteristic parameters representing a particle shape of the effective pigment include particle size, circularity, outline condition, and number of notches,
   the outline condition being a number of peaks and valleys in a two-dimensional contour profile obtained by plotting a distance from a centroid of one particle of the effective pigment in an image to pixels on an outline of the particle, in the order of tracing the outline, and
   the number of notches being a number of deep valleys in the two-dimensional contour profile.

7. The method according to claim 1 wherein
   the dominant color hue angle is a mode of a hue angle histogram of pixels in an image of one particle of the effective pigment in the HSI color space,
   the intensity of the dominant color is an average intensity of pixels having the dominant color hue angle, and
   the saturation of the dominant color is an average saturation of pixels having the dominant color hue angle.

8. The method according to claim 7 wherein the characteristic parameters comprise at least one characteristic parameter representing a particle shape of the effective pigment.

9. The method according to claim 1 wherein identifying the effective pigment comprises applying a neural network that uses the characteristic parameters of a particular effective pigment as input units and information regarding the particular effective pigment as output units.

10. The method according to claim 9 wherein output values of the output units are real numbers, and a predetermined number of effective pigments are selected from the database according to the output values of the output units.

11. The method of claim 1, wherein the characteristic parameters comprise at least one characteristic parameter representing a particle shape of the effective pigment.

12. The method of claim 1, wherein the characteristic parameters comprises at least one characteristic parameter representing a particle size of the effective pigment.

13. An effective pigment identification system comprising:
an image-capturing device for imaging an effective pigment and obtaining first image data, wherein the imaged effective pigment imparts a design effect that changes appearance with angle of observation;
a characteristic parameter detector for background processing the first image data, extracting an image of only one particle of the effective pigment as second image data, then image processing the second image data to computer characteristic parameters of the effective pigment; and
a recording device for storing a database of information indicative of various types of effective pigments respectively associated with image data and characteristic parameters of the various kinds of effective pigments, wherein the various types of effective pigments stored in the database each impart a design effect that changes appearance with angle of observation, wherein the image data of the various kinds of effective pigments each contain only one particle and the characteristic parameters of the various kinds of effective pigments are obtained by conducting said extracting and said computing;
wherein the characteristic parameter detector identifies the effective pigment based at least in part on the computed characteristic parameters and the database, and
wherein the identified effective pigment imparts a design effect that changes appearance with angle of observation, the characteristic parameters including parameters representing a color of the effective pigment, the parameters representing the color of the effective pigment including sine and cosine values of a dominant color hue angle, intensity of the dominant color, and saturation of the dominant color.

14. The system of claim 13, wherein the characteristic parameters comprise at least one characteristic parameter representing a particle shape of the effective pigment.

15. The system of claim 13, wherein the characteristic parameters comprises at least one characteristic parameter representing a particle size of the effective pigment.

16. A non-transitory computer-readable medium storing computer-executable instructions which, when executed cause a system to perform a method of identifying an effective pigment, the method comprising:
imaging the effective pigment to obtain first image data, wherein the imaged effective pigment imparts a design effect that changes appearance with angle of observation;
subjecting the obtained image data to background processing and extracting image data concerning a region containing only one particle of the effective pigment as second image data;
calculating characteristic parameters of the effective pigment from the second image data, the characteristic parameters including parameters representing a color of the effective pigment, the parameters representing the color of the effective pigment including sine and cosine values of a dominant color hue angle, intensity of the dominant color, and saturation of the dominant color; and
identifying the effective pigment based at least in part on the extracted characteristic parameters and a pre-prepared database that stores information indicative of various kinds of effective pigments respectively associated with image data and characteristic parameters of the various kinds of effective pigments,
wherein the identified effective pigment imparts a design effect that changes appearance with angle of observation and the various kinds of effective pigments stored in the database each impart a design effect that changes appearance with angle of observation, and
wherein the image data of the various kinds of effective pigments each contain only one particle and the characteristic parameters of the various kinds of effective pigments are obtained by conducting said subjecting and said calculating, the characteristic parameters including parameters representing a color of the effective pigment, the parameters representing the color of the effective pigment including sine and cosine values of a dominant color hue angle, intensity of the dominant color, and saturation of the dominant color.

17. The non-transitory computer-readable medium of claim 16 further comprising the pre-prepared database.

18. The non-transitory computer-readable medium of claim 16, wherein the characteristic parameters comprise at least one characteristic parameter representing a particle shape of the effective pigment.

19. The non-transitory computer-readable medium of claim 16, wherein the characteristic parameters comprises at least one characteristic parameter representing a particle size of the effective pigment.

20. An effective pigment identification system comprising:
a camera configured to image an effective pigment and obtain first image data, wherein the imaged effective pigment imparts a design effect that changes appearance with angle of observation;
a database configured to store information indicative of various types of effective pigments respectively associated with image data and characteristic parameters of the various kinds of effective pigments, wherein the various types of effective pigments stored in the database each impart a design effect that changes appearance with angle of observation; and
a processor configured to:
extract an image of only one particle of the effective pigment from the first image data as second image data,
compute characteristic parameters of the effective pigment from the second image data, and
identify the effective pigment based at least in part on the computed characteristic parameters and the database, wherein the identified effective pigment imparts a design effect that changes appearance with angle of observation,
wherein the image data of the various types of effective pigments each contain only one particle and the characteristic parameters of the various types of effective pigments are obtained by said processor configured to extract and compute, the characteristic parameters including parameters representing a color of the effective pigment, the parameters representing the color of the effective pigment including sine and cosine values of a dominant color hue angle, intensity of the dominant color, and saturation of the dominant color.

* * * * *

UNITED STATES PATENT AND TRADEMARK OFFICE
CERTIFICATE OF CORRECTION

PATENT NO. : 8,290,275 B2
APPLICATION NO. : 11/621505
DATED : January 9, 2007
INVENTOR(S) : Keisuke Sai, Yutaka Masuda and Yoshinori Arai It is certified that error appears in the above-identified patent and that said Letters Patent is hereby corrected as shown below:

In the Claims:

In Column 16, Line 7, Claim 1, change "representing;" to --representing--.

In Column 17, Line 21, Claim 13, change "computer" to --compute--.

Signed and Sealed this
Eighteenth Day of June, 2013

Teresa Stanek Rea
*Acting Director of the United States Patent and Trademark Office*